(12) United States Patent
Menta et al.

(10) Patent No.: US 6,596,889 B1
(45) Date of Patent: Jul. 22, 2003

(54) NITRATES OF BIS-PLATINUM COMPLEXES WITH POLYAMINE LIGANDS

(75) Inventors: Ernesto Menta, Monza (IT); Giovanni Da Re, Monza (IT)

(73) Assignee: Novuspharma S.p.A., Milan (IT)

( * ) Notice: Subject to any disclaimer, the term of this patent is extended or adjusted under 35 U.S.C. 154(b) by 0 days.

(21) Appl. No.: 10/019,271

(22) PCT Filed: Jul. 5, 2000

(86) PCT No.: PCT/EP00/06288

§ 371 (c)(1),
(2), (4) Date: Feb. 13, 2002

(87) PCT Pub. No.: WO00/04132

PCT Pub. Date: Jan. 18, 2001

(30) Foreign Application Priority Data

Jul. 9, 1999 (IT) .................................... MI99A001508

(51) Int. Cl.$^7$ ............................ C07F 15/00; A61K 31/28
(52) U.S. Cl. ..................................... 556/137; 514/492
(58) Field of Search ........................... 556/137; 514/492

(56) References Cited

U.S. PATENT DOCUMENTS

| | | | | |
|---|---|---|---|---|
| 6,022,892 A | * | 2/2000 | Farrell et al. ................ | 514/493 |
| 6,060,616 A | * | 5/2000 | Farrell et al. ................ | 556/137 |
| 6,130,245 A | * | 10/2000 | Shaw ........................... | 514/492 |
| 6,313,333 B1 | * | 11/2001 | Da Re et al. ................. | 556/137 |

FOREIGN PATENT DOCUMENTS

| | | |
|---|---|---|
| EP | 0214862 | 3/1987 |
| WO | WO 98/03519 | 1/1998 |

* cited by examiner

*Primary Examiner*—Porfirio Nazario-Gonzalez
(74) *Attorney, Agent, or Firm*—Rothwell, Figg, Ernst & Manbeck

(57) ABSTRACT

Nitrates of Bis-platinum complexes with polyamine ligands of formula (I) having antitumor activity and pharmaceutical compositions containing said compounds as active principles.

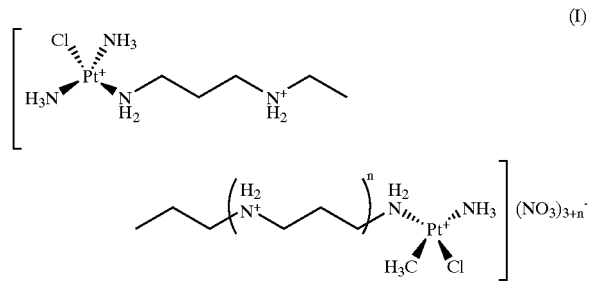

n = 0, 1

6 Claims, 2 Drawing Sheets

1a

1b

2a

2b

NITRATES OF BIS-PLATINUM COMPLEXES WITH POLYAMINE LIGANDS

CROSS REFERENCE TO RELATED APPLICATION

Figure 1:
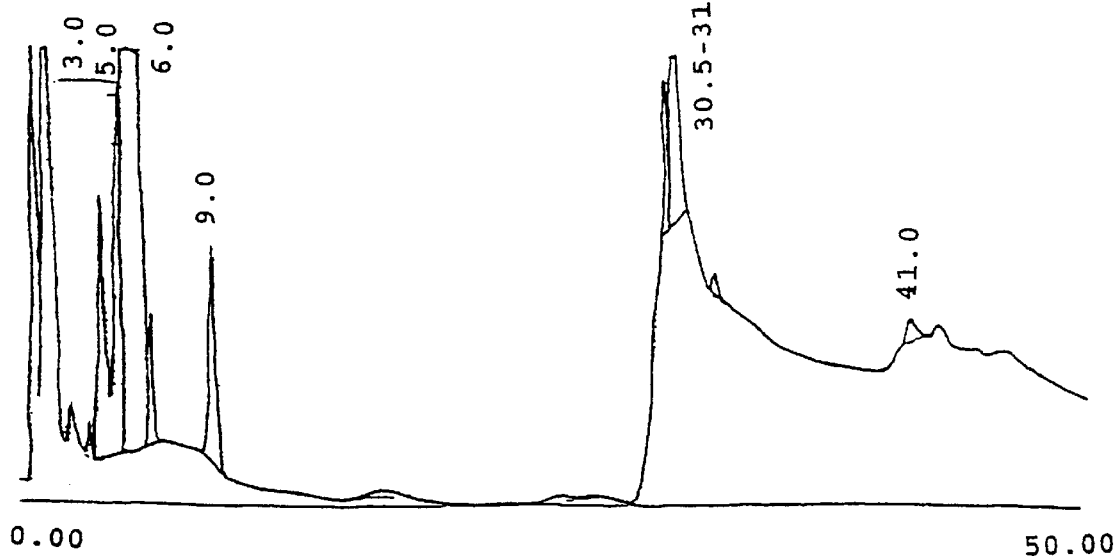
Figure 1:
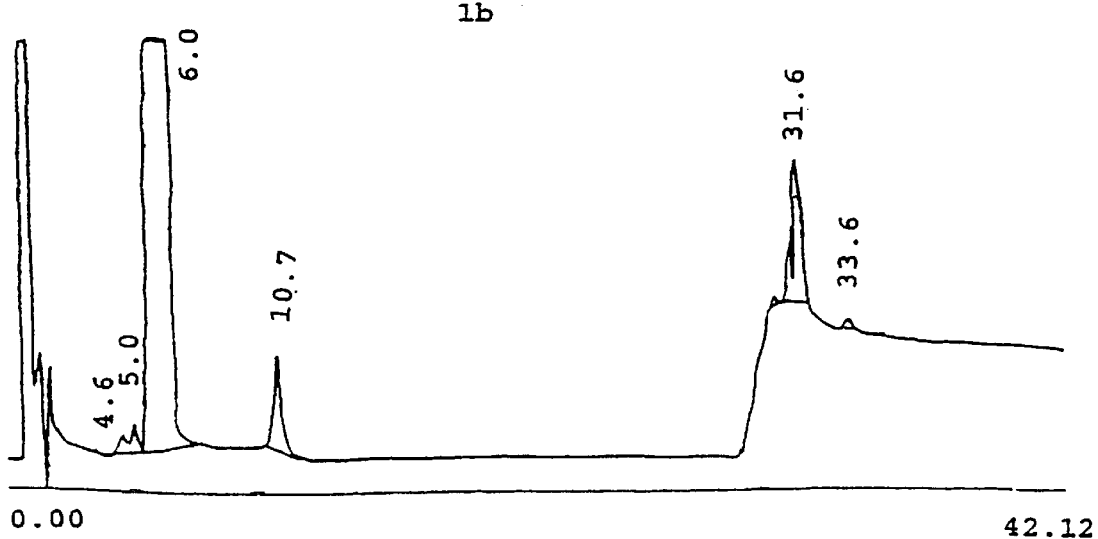

This application is a 35 U.S.C. 371 National Phase Entry Application from PCT/EP00/06288, filed Jul. 5, 2000, and designating the U.S.

The present invention relates to compounds of formula (I),

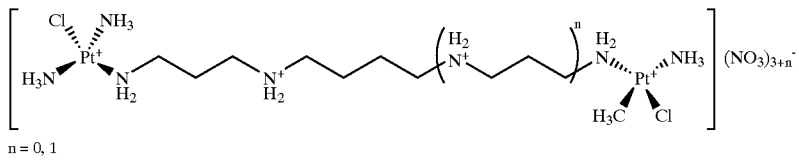

n = 0, 1 in which n is zero or the integer 1.

Furthermore, the present invention relates to the pharmaceutical compositions containing said compounds as active principles.

The compounds of formula (I) are bis-platinum complexes with polyamine ligands having antitumor activity against both resistant and non-resistant cells to cisplatin.

TECHNOLOGICAL BACKGROUND

WO 98/03519 discloses bis-platinum complexes with polyamine ligands (spermine and spermidine) which are the same as those of formula (I), but are salified with chloride anions instead of nitrate ones.

Said compounds, respectively represented by the formula:

A

Compound A

B

Compound B

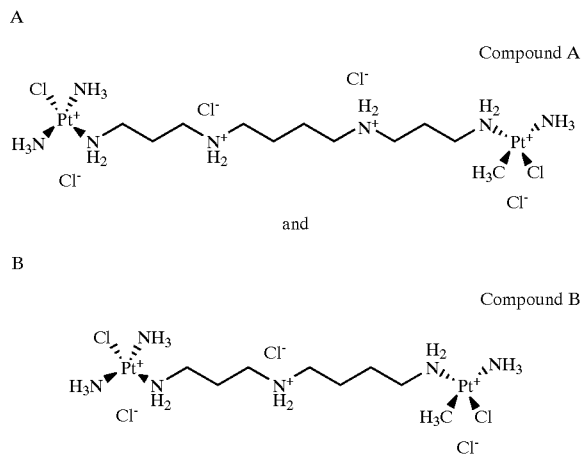

have potent cytotoxic activity against cis-platinum resistant tumour cells, such as the L1210/CDDP and A2780/CDDP cell lines. The in vitro activity was further confirmed in vivo, in murine tumors experimental models.

The disclosed compounds have not, however, ideal solubility, stability and purity characteristics in view of the envisaged pharmaceutical use.

DISCLOSURE OF THE INVENTION

It has now been found that the compounds of formula (I), which are the nitrates of the above mentioned compounds A and B, have improved solubility, stability and purity characteristics, so that they are particularly suitable to the formulation of pharmaceutical compositions, above all for the parenteral use.

The compound of the invention of formula I in which n is 1 (Compound 1, spermine derivative) and the compound of formula I in which n is zero (Compound 2, spermidine derivative), can be prepared starting from the corresponding A and B chloride salts, respectively, by reaction with alkaline nitrates or silver nitrate in aqueous solutions.

Sodium nitrate is preferably used in high concentrations, typically ranging from 2 to 5 M, in the presence of strong inorganic acids such as HCl, in concentrations ranging from about 1 to about 10 mM. The nitrate salts precipitate in the form of crystalline solids which can be washed with alcoholic or water-alcoholic solutions. The preparation of the starting Compound A and Compound B chloride salts is reported in examples 16 and 14, respectively, of WO 98/03519 which is herein incorporated for reference.

The compounds of formula (I), when administered to humans and animals bearing tumors which can be treated with cis-platin or to which they are resistant, at doses ranging from 0.1 mg to 1.2 g per square metre body area, are capable of inducing the regression of said tumors.

More generally, the compounds of the invention can be used for the treatment of the same pathological conditions for which cis-platin is used. This includes the treatment of tumors, sensitization or enhancement of radiations [Douple et al., Cis-platin Current Status and Developments, Ed. A. W. Prestayk et al., Academic Press, 125 (1980); Douple et al., Platinum Metals Res., 29; 118 (1985)] and the treatment of parasitic diseases such as African sleeping sickness [Farrell et al., Biochem. Pharmacol., 33, 961 (1984)].

Therefore, another object of the present invention consists of pharmaceutical compositions containing a therapeutically effective amount of at least one compound of formula (I) in mixture with conventional carriers and excipients.

The effective dosage of the compounds of the invention can be determined by expert clinicians according to conventional methods. The relationship between the dosages used for animals of various species and sizes and those for humans (on the basis of $mg/m^2$ body area) is described by Freirech et al., Quantitative Comparison of Toxicity of Anticancer Agents in Mouse, Rat, Hamster, Dog, Monkey and Man, Cancer Chemother. Rep., 50, N. 4, 219–244 (1986).

Usually, however, the patient will receive doses from 0.1 to 1200 mg/kg body weight of the complex, with a dosage regimen which will vary depending on various factors which are well known to the expert clinicians.

The treatment regimen can suitably be varied, as it is well known to the expert clinician, according to the type of tumor to be treated and the conditions of the patient.

The compounds of the invention will be administered through the parenteral or oral routes.

The pharmaceutical compositions for the parenteral administration comprise sterile saline solutions, as defined above, or sterile powders for the extemporary preparation of the solutions, as well as oily preparations for intramuscular (im) or intraperitoneal (ip) administrations.

The compounds of the invention are preferably administered as sterile aqueous solutions, optionally containing sodium chloride in suitable concentration (0.1–0.9 mg/ml). The solutions are preferably administered by the intravenous (iv) or intra-arterial (ia) routes, even though other administration forms can be used in particular cases.

Useful pharmaceutical compositions for the oral administration can be syrups or similar liquid forms, as well as solid forms such as tablets, capsules and the like.

The pharmaceutical compositions according to the present invention are prepared following known methods, such as those reported in Remington's Pharmaceutical Sciences Handbook, XVII Ed., Mack Pub., N.Y., U.S.A.

Sometimes it can prove advantageous to administer the platinum complexes of the present invention together with one or more agents which enhance the antitumor activity or relieve the undesirable side effects which may be associated with the platinum complex therapy. For example, the platinum complexes of the present invention can be administered together with reduced glutathione, as disclosed in GB 2,174, 905 and in U.S. Pat. No. 4,871,528.

Furthermore, it can be advantageous to administer the platinum complexes of the present invention in combination with other platinum complexes having antitumor activity.

Therefore, a further object of the present invention consists of pharmaceutical compositions containing at least one compound of formula (I) in combination with a platinum complex having antitumor activity.

A further object of the present invention consists of the use of the compounds of formula (I) for the preparation of pharmaceutical compositions for the treatment of mammals bearing tumors which can be treated with cis-platinum or resistant to cis-platinum.

The invention is further illustrated by the following examples.

EXAMPLE 1

Preparation of bis{trans(diammine)(chloro) Platinum (II)}-$\mu$-(1,8-diamino-4-azaoctane-$N^1,N^8$) dinitrate salt.$HNO_3$, (Compound 2)

A solution of bis {trans(diammine)(chloro)platinum(II)}-$\mu$-(1,8-diamino-4-azaoctane-$N^1$, $N^8$) dichloride salt.HCl prepared according to example 14 of WO 98/03519, (0.306 g, 0.391 mmol) in 8 mM HCl (15 ml) at room temperature is added with active charcoal (Norit A, 50 mg) and the mixture is stirred for 30 minutes. Charcoal is filtered off and the resulting clear filtrate is cooled to 10° C. A 4N NaNO$_3$ solution (1.5 mL, 5.87 mmol) is added and within a few minutes a white solid precipitates. The mixture is stirred for 3 hours, then the precipitated solid is filtered, washed with $H_2O$/MeOH 1:1 (2×3 mL), with MeOH (3 mL) and dried under vacuum (35° C., 2 h) to obtain 0.25 g (74% yield) of bis{trans(diammine) (chloro)platinum(II)}-$\mu$-(1,8-diamino-4-azaoctane-$N^1$, $N^8$) dinitrate salt.$HNO_3$, (Compound 2).

Analytical Data $^1$H-NMR ($\delta$; $D_2O$): 1.75 (bt, 4H); 2.15 (m, 2H); 2.75 (m, 4H); 3.10 (bt, 4H); HPLC: rt (Compound 2)=6 min (97.2 area%); Elemental analysis: calculated %: C, 9.76; H, 3.74; N, 16.26; Cl 8.23; Pt 45.29. found %: C, 9.84; H, 3.76; N, 15.67; Cl 9.04; Pt 45.15.

EXAMPLE 2

Preparation of bis{Trans (diammine) (Chloro) platinum(II)}-$\mu$-(1,12-diamino-4,9-diazadodecane-$N^1,N^{12}$) dinitrate Salt.$2HNO_3$, (Compound 1)

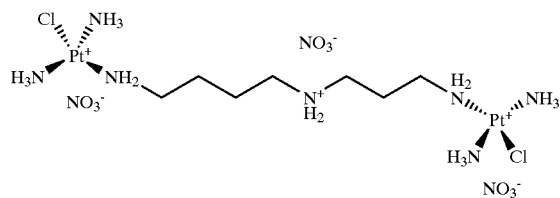

A solution of bis{trans(diammine)(chloro)platinum(II)}-$\mu$-(1,12-diamino-4,9-diazadodecane-$N^1$, $N^{12}$) dichloride salt.2HCl, prepared according to Example 16 of WO 98/03519 (0.71 g, 0.811 mmol) in 8mM HCl (60ml) at room temperature is added with active charcoal (Norit A, 50 mg) and the mixture is stirred for 30 minutes. Charcoal is filtered off and the resulting clear filtrate is cooled to 10° C. A solution of 4N NaNO$_3$ (3 mL, 12 mmol) is added and within a few minutes a white solid precipitates. The mixture is stirred for 13 hours, then the precipitated solid is filtered, washed with $H_2O$/MeOH 1:1 (2×3 mL), with MeOH (3 mL) and dried under vacuum (35° C., 2h) to obtain 0.6 g (75% yield) of bis{trans(diammine)(chloro)platinum(II)}-$\mu$-(1,12-diamino-4,9-diazadodecane-$N^1$, $N^{12}$) di-nitrate salt.$2HNO_3$, (Compound 1).

Analytical Data $^1$H-NMR ($\delta$; $D_2O$): 1.75 (m, 4H); 2.10 (bq, 4H); 2.80 (bq.4H); 3.15 (bt, 8H); HPLC: rt (Compound 1)=11 min (98.8 area%); Elemental analysis: calculated %: C, 12.24; H, 4.11; N, 17.12; Cl 7.22; Pt 39.65. found %: C, 12.43; H, 4.09; N, 17.02; Cl 7.26; Pt 39.71.

EXAMPLE 3

FIG. 1a shows the chromatographic profile obtained with bis{trans(diammine)(chloro)platinum(II))}-$\mu$-(1,8-diamino-4-azaoctane-$N^1$, $N^8$) dichloride salt.HCl, (Compound B, prepared as described in example 14 of WO 98/03519) compared with the chromatographic profile of figure 1b obtained with the corresponding bis{trans(diammine) (chloro)platinum(II)}-$\mu$-(1,8-diamino-4-azaoctane-$N^1$, $N^8$) dinitrate salt.$HNO_3$ (Compound 2) of example 1, using the following chromatographic system:

column: Lichrospher RP8 (5 $\mu$m), 125×4 mm

| | | |
|---|---|---|
| eluent A: | H$_2$O/CH$_3$CN 80/20 sodium octanesulfonate (2.5 g/L) pH 2.7 with 85% H$_3$PO$_4$ | |
| eluent B: | H$_2$O/CH$_3$CN 45/55 sodium octanesulfonate (2.5 g/L) pH 2.7 with H$_3$PO$_4$ 85% | |
| Gradient: | eluent A/eluent B 50/50 0–24') to eluent A/eluent B 25/75 (26'–50') | |
| flow: | 1 mL/min | |
| detection | UV (225 nm) | |

EXAMPLE 4

Figure 2:
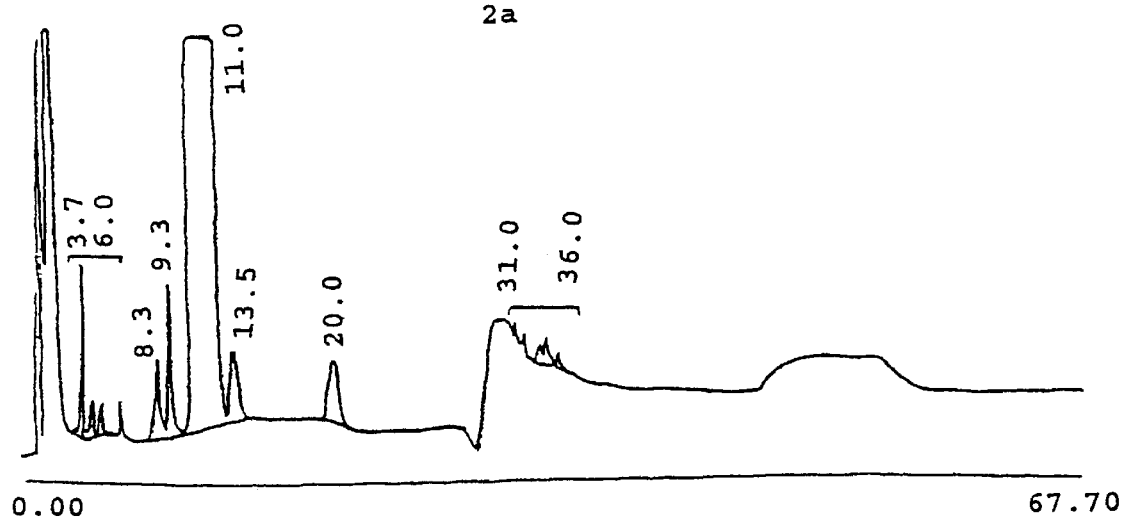
Figure 2:
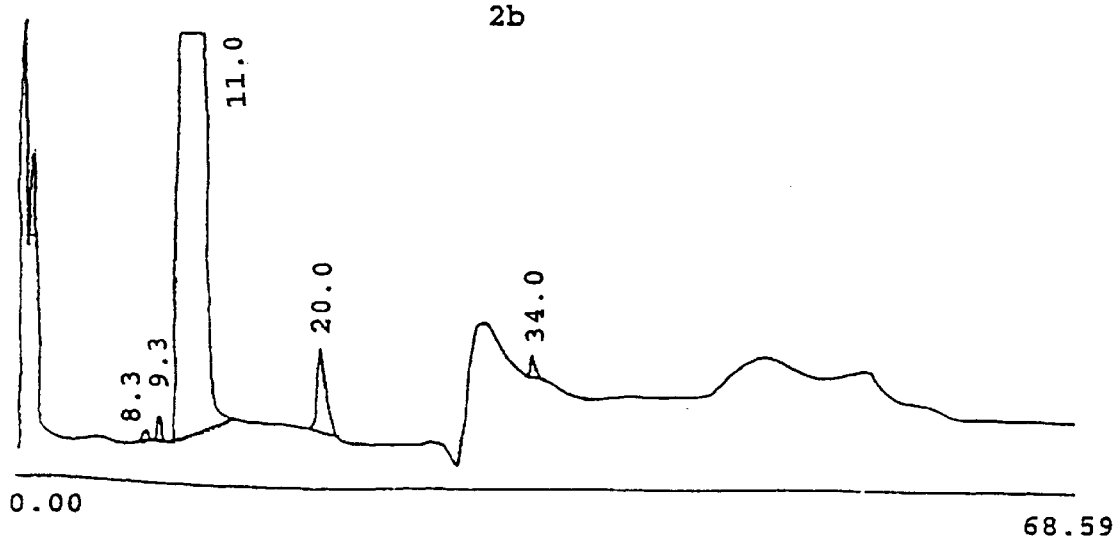

FIG. 2a shows the chromatographic profile obtained with bis{trans(diammine)(chloro)platinum(II)}-μ-(1,12-diamino-4,9-diazadodecane-N$^1$, N$^{12}$)dichloride salt.2HCl, (Compound A, prepared as described in example 16 of WO 98/03519) compared with the chromatographic profile of FIG. 2b obtained with the corresponding bis{trans(diammine)(chloro)platinum(II)}-μ-(1,12-diamino-4,9-diazadodecane-N$^1$, N$^{12}$) dinitrate salt.2HNO$_3$ (Compound 1), of example 2, using the chromatographic system described in example 3.

EXAMPLE 5

The following table reports the HPLC data concerning the stability of Compound 1 and of Compound A (prepared as described in example 16 of WO 98/03519) following heating at 40° C. for 12 days under atmospheric pressure.

The used chromatographic method is that described in Example 3 and Example 4. The values of retention times are in percent area.

| | Compound 1 | | Compound A | |
|---|---|---|---|---|
| Retention times (min) | t = 0 | 12 days 40° C. | t = 0 | 12 days 40° C. |
| MAIN IMPURITIES | | | | |
| mean peak | 98.5 | 98.4 | 92.5 | 89.8 |
| 7 | 0.1 | 0.1 | 0.1 | 0.8 |
| 8 | 0.1 | 0.1 | 0.2 | 1.6 |
| 12 | 0.1 | 0.2 | 0.3 | 0.6 |

-continued

| | Compound 1 | | Compound A | |
|---|---|---|---|---|
| Retention times (min) | t = 0 | 12 days 40° C. | t = 0 | 12 days 40° C. |
| 14 | 0.8 | 0.9 | 1.3 | 0.8 |
| 30 | <0.1 | <0.1 | 2.3 | 2.8 |
| 31 | n.d.* | 0.2 | 0.7 | 1.7 |

*n.d. = not detectable

What is claimed is:

1. A compound of formula (I),

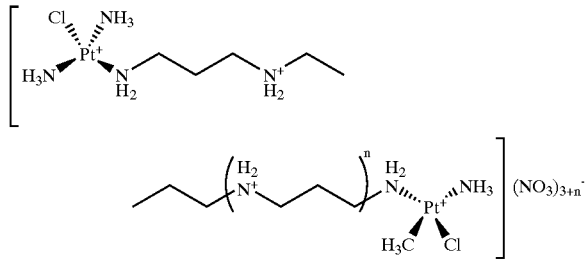

in which n is zero or the integer 1.

2. A process for the preparation of a compound of claim 1, comprising reacting the corresponding chlorides in solutions in strong organic acids with an aqueous solution of an alkaline or silver nitrate.

3. A process as claimed in claim 2, in which the inorganic acid is hydrochloric acid in 1 to 10 mM concentration.

4. A process as claimed in claim 2, in which the alkaline nitrate is sodium nitrate.

5. A Pharmaceutical composition containing as active ingredient a therapeutically effective amount of at least one compound of claim 1, together with conventional carriers and excipients.

6. A method of treating in a patient a tumor treatable with or resistant to cis-platinum, comprising administering to the patient an anti-tumor effective amount of a compound of claim 1.

* * * * *